United States Patent
Fink et al.

(10) Patent No.: US 10,265,529 B2
(45) Date of Patent: *Apr. 23, 2019

(54) APPARATUS FOR ELECTRICAL STIMULATION OF A CELL AND METHOD OF USE

(71) Applicant: ARIZONA BOARD OF REGENTS ON BEHALF OF THE UNIVERSITY OF ARIZONA, Tucson, AZ (US)

(72) Inventors: Wolfgang Fink, Montrose, CA (US); Erich Schmid, Tuebingen (DE)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/867,131

(22) Filed: Jan. 10, 2018

(65) Prior Publication Data
US 2018/0140844 A1    May 24, 2018

Related U.S. Application Data

(63) Continuation of application No. 14/424,966, filed as application No. PCT/US2013/057098 on Aug. 28, 2013, now Pat. No. 9,867,988.

(60) Provisional application No. 61/743,206, filed on Aug. 29, 2012, provisional application No. 61/744,555, filed on Sep. 28, 2012.

(51) Int. Cl.
  *A61N 1/36* (2006.01)
  *A61N 1/05* (2006.01)

(52) U.S. Cl.
  CPC ....... *A61N 1/36182* (2013.01); *A61N 1/0543* (2013.01); *A61N 1/36046* (2013.01); *A61N 1/0529* (2013.01); *A61N 1/0551* (2013.01); *A61N 1/36067* (2013.01); *A61N 1/36082* (2013.01); *A61N 1/36185* (2013.01)

(58) Field of Classification Search
  CPC ............ A61N 1/36182; A61N 1/36046; A61N 1/0543; A61N 1/0529; A61N 1/36082; A61N 1/36185; A61N 1/36067; A61N 1/0551
  See application file for complete search history.

(56) References Cited

U.S. PATENT DOCUMENTS

2011/0172725 A1* 7/2011 Wells ................ A61N 1/36017
    607/3
2011/0307032 A1* 12/2011 Goetz ............... A61N 1/36185
    607/59

OTHER PUBLICATIONS

Fink, "Stochastic Optimization Framework (SOF) for Computer-Optimized Design, Engineering, and Performance of Multi-Dimensional Systems and Processes," Proc. SPIE, 2008, vol. 6960, 69600N; DOI: 10.1117/12.784440.*

* cited by examiner

Primary Examiner — Rex R Holmes
(74) Attorney, Agent, or Firm — Don D. Cha; Hamilton DeSanctis & Cha, LLP

(57) ABSTRACT

This invention provides an apparatus for electrically stimulating a cell and a method for using the same. In particular, the apparatus of the invention comprises an array of electrodes and a controller for actuating individual electrodes.

20 Claims, 5 Drawing Sheets

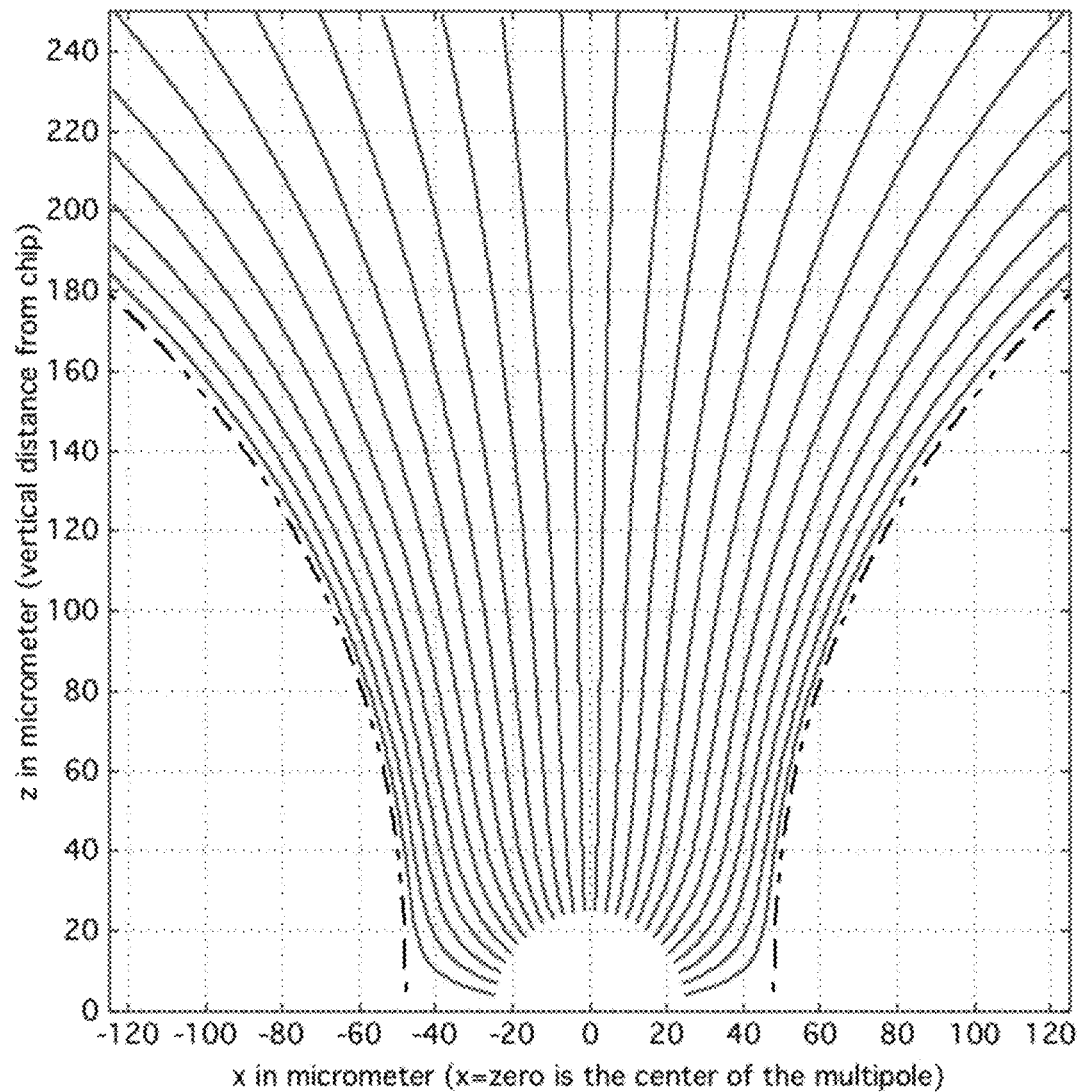
FIGUE 3B

APPARATUS FOR ELECTRICAL STIMULATION OF A CELL AND METHOD OF USE

CROSS-REFERENCE TO RELATED APPLICATIONS

This is a continuation application of U.S. patent application Ser. No. 14/424,966, filed Feb. 27, 2015, now U.S. Pat. No. 9,867,988, issued Jan. 16, 2018, which is a 35 U.S.C. § 371 U.S. National Stage Application of PCT Patent Application No. PCT/US13/57098, filed Aug. 28, 2013, which claims priority benefits of U.S. Provisional Application Nos. 61/743,206, filed Aug. 29, 2012, and 61/744,555, filed Sep. 28, 2012, all of which are incorporated herein by reference in their entirety.

FIELD OF THE INVENTION

This invention relates to an apparatus for electrically stimulating a cell and a method for using the same. In particular, the apparatus of the invention comprises an array of electrodes and a controller for actuating individual electrodes. The controller is configured to: (i) actuate an electrode to produce a transverse stimulating electric field, (ii) actuate an electrode to produce a stimulating electric field and another electrode as a field shaping electrode to produce a guiding field; (iii) or a combination of both.

BACKGROUND OF THE INVENTION

Currently, there is a tremendous interest in treating a subject having a clinical condition associated with impairment in electrical stimulation of cells or tissues. It should be appreciated that as used herein, in general, the term "a clinical condition associated with impairment in electrical stimulation" refers to a manifestation of a clinical condition due to improperly functioning neurons or retina. Such improper function can be due to impaired transmission of a signal from one cell to another cell (e.g., typically to an adjacent cell), lack of cell function even in the presence of a properly transmitted signal from another cell, or due to cell death or disrupted pathways.

Many prostheses have been developed to treat spinal cord injury by implanting an artificial electric stimulation device. Exemplary clinical conditions associated with impairment in electrical stimulation of cells and/or tissues include, but are not limited to, neural cell damage or impaired neural cell function such as retinal damage (such as retinitis pigmentosa, retinal detachment, diabetic retinopathy, and macular degeneration), optic neuropathy, glaucoma, stroke, spinal cord injury, peripheral nerve injury, demyelinating disease (such as multiple sclerosis), and central nervous system injury secondary to ischemia, compression, nerve injury, infection affecting nerve cell function, elevated intracranial pressure, elevated intraocular pressure (ocular hypertension), congenital and hereditary genetic diseases associated with impaired nerve cell function, toxic neuropathy and encephalopathy, neurological sequelae of systemic diseases such as chronic arterial hypertension, diabetes, HIV infection, systemic lupus, coagulation disorders, Parkinson's disease, Alzheimer's disease, prion disease, and paralysis. Retinal damage or impaired retinal function can lead to diminished sight and blindness. And, as the age of the general population increases, the number of people suffering from diminished sight due to these causes increases.

Functions of some cells can be replaced or approximated by providing an appropriate electrical stimulation to cells they are connected to. It should be appreciated that as used herein, a clinical condition associated with electrical stimulation impairment refers to any clinical condition that manifests itself due to an improper or missing signaling of one cell to another cell, often an adjacent cell. Several devices have been developed to attempt to restore vision loss due to retinal damage. For example, photovoltaic devices, which are attached to a portion of a retina, have been developed to replace the signals that normally emerge from rods and/or cones in a healthy eye within the retina by stimulating functioning cells. Although such devices may provide some stimulation, the devices suffer from several drawbacks.

Vision impairment can be caused by numerous factors. While many vision impairments can be corrected by corrective eyewear and surgery, not all vision impairment can be treated by such relatively simple methods. For example, some vision impairments involve problems with the light-processing functions of the eye. These problems are usually caused by abnormalities of the retina and macula such as retinitis pigmentosa and age-related macular degeneration. Vision impairments due to these causes cannot be addressed with corrective eyewear or eye surgery. It is estimated that globally over one and a half million people have progressive vision loss as a result of retinitis pigmentosa, the primary cause of inherited blindness.

To address such vision impairment, research on retinal implants has been ongoing for about two decades. One area of such research is to restore a small part of vision to people suffering from blindness due to retinitis pigmentosa or due to age related macula degeneration. One of the conventionally available devices for treating vision impairment is a chip with an array of electrodes that is placed into an epi-retinal, sub-retinal, or supra-choroidal position. With this device, electric currents emerging from the electrodes are seen by the blind person as small phosphenes. Thus, electrodes serve as pixels for presenting an image. Unfortunately, despite some encouraging results the goal of presenting a gray-scaled picture with a thousand or more pixels has not yet been reached. Other devices that have been developed include optic nerve implants, lateral geniculate nucleus implants, cortical implants, as well as non-invasive remedies such as electric tongue stimulators, and tactile stimulators.

Problems associated with currently available retinal implants include use of too simple time profiles of the electric stimulation signals. Currently, the most common time profile is the monophasic rectangular voltage pulse, which yields a biphasic current pulse. Or the biphasic rectangular voltage pulse, which yields a triphasic current pulse. Such pulses lead to the depolarization (or hyperpolarization) of a cell membrane in the first phase of the current, and to a polarization of opposite sign in the next phase of the current.

Another shortcoming in many conventional retinal implants is using only one electrode per pixel. Moreover, many research groups are using a common remote counter electrode that is far away from the electrode array. While one group in Australia is using six (6) counter electrodes around a center electrode on a hexagonal grid and, by current splitting, this group also uses a common remote counter electrode, i.e., far away from the electrode array. See Lovell et al., *Engineering in Medicine and Biology Society*, 2005, 27th Annual International Conference of the IEEE—EMBS, 2005, pp. 5242-5245, 17-18 Jan. 2006; doi:10.1109/IEMBS.2005.1615661]. One of the key problems associated with using counter electrodes at infinity, is that it leads to cross-talk. See, for example, Schmid et al., Electric Stimulation of the Retina; 2010, arXiv:1012.5958v1 [q-bio.NC].

Yet another problem associated with conventional retinal implants involves too little effort for shaping the electric field (or current). Simultaneous firing of neighboring electrodes leads to bunching of field lines, i.e., increased density of field lines above the electrodes. But it also means undesired cross-talk between neighboring electrodes.

Therefore, there is a need for a new apparatus and method for treating a clinical condition associated with an improper electrical signaling of a cell and/or tissue.

SUMMARY OF THE INVENTION

Some aspects of the invention provide an apparatus and a method for electrically stimulating a cell. Often the apparatus and the method of the invention are used to electrically stimulate cells in a subject. Such cell stimulation can be used to treat a variety of clinical conditions associated with an impaired electrical activity of a cell. The term "impaired electrical activity of a cell" includes missing or disrupted signaling from one cell to another. Exemplary clinical conditions that can be treated using the apparatus and the method of the invention disclosed herein include, but are not limited to, vision impairment, stroke, spinal cord injury, peripheral nerve injury, demyelinating disease, paralysis or a combination thereof.

While the apparatus and the method of the invention can be used to directly stimulate a cell with impaired electrical activity, typically the apparatus and the method of the invention are used to replace impaired activity by electrical stimulation of intact cells. Often the remaining intact (i.e., functioning) cells and intact pathways are stimulated to "replace" or approximate the function of the cells that have impaired electrical activity or impaired electrical pathways. For example, some clinical conditions, such as blindness and paralysis, are caused by the loss of cells (e.g., rods or cones) or by a disconnected neural pathway (paralysis). The apparatus and the method of the present invention are typically used to stimulate the remaining intact cells and intact pathways to "replace" or approximate the function of the dead cells or disconnected pathways.

In one particular embodiment, the apparatus of the invention comprises:

an array of electrodes configured to be implanted in a subject, wherein said array of electrodes comprises an arrangement of individual electrodes; and a controller operatively connected to said array of electrodes for actuating the individual electrodes, wherein said controller is configured to actuate at least one of the individual electrodes as a stimulating electric field producing electrode and at least one of the individual electrodes as a counter electrode having an opposite polarity relative to said stimulating electric field producing electrode, and wherein said controller is further configured to actuate said stimulating electric field producing electrode to produce a transverse stimulation electric field to the cell.

Yet in another embodiment, the apparatus of the invention comprises:

an array of individual electrodes configured to be implanted in a subject; and a controller operatively connected to said array of individual electrodes and adapted for actuating said individual electrodes, wherein said controller is configured to actuate at least one of the individual electrodes as a stimulating electric field producing electrode to produce a cell stimulating electric field and at least one other of said individual electrodes as a field shaping electrode to produce a guiding electric field.

In some embodiments, the presence of said guiding electric field increases the strength of said stimulating electric field to the cell relative to the strength of said stimulating electric field to the cell in the absence of said guiding electric field. It should be appreciated that the increase in strength of the stimulating field is because the guiding electric field pushes or forces the stimulating electric field into the desired target area of the cell.

Another aspect of the invention provides a method for treating a clinical condition associated with an impaired electrical activity of a cell in a subject by using an apparatus of the invention disclosed herein. Such a method typically includes implanting the apparatus of the invention to the subject at or near the site of a cell with impaired electrical activity. Typically, the apparatus of the invention is used to electrically stimulate functioning or "intact" cells and/or pathways to replace, substitute or approximate the function of the cells that has electrical activity impairment.

In one particular embodiment, the method of invention includes actuating said stimulating electric field producing electrode using said controller to produce a transverse stimulating electrical field from said stimulating electric field producing electrode thereby electrically stimulating the cell to treat the clinical condition associated with impaired electrical activity of a cell in said subject.

Yet in another embodiment, the method of the invention includes actuating said stimulating electric field producing electrode and stimulating electric field shaping electrode using said controller to produce a stimulating electric field thereby electrically stimulating a cell within said subject to treat the clinical condition associated with impaired electrical activity of a cell.

BRIEF DESCRIPTION OF THE DRAWINGS

FIG. 2A is a top view of the relevant electrodes on the array. The blue (inner, i.e., field shaping) electrodes are the 4 dipoles producing the ridge, the red (outer) electrodes are the stimulating electric field producing electrodes. FIG. 2B shows the stimulating electric field in red on a plot screen vertical to the array with a base line including the stimulating electric field producing electrodes. The broken line is a separatrix, separating the stimulating electric field (above the separatrix) from the guiding field (underneath the separatrix). The semicircles around the stimulating electric field producing electrodes have no physical meaning; they are introduced for plotting reasons. The guiding field lines of the field shaping electrodes shown in blue in FIG. 2A are not plotted in FIG. 2B. FIG. 2C shows guiding field lines (middle) and stimulation electric field lines (above and around the middle).

FIG. 3B is a plot of the stimulating electric field produced and shaped by the multipole configuration of FIG. 3A. The guiding field is not plotted in FIG. 3B. The broken line is a separatrix, separating the stimulating electric field from the guiding field.

DETAILED DESCRIPTION OF THE INVENTION

Definition

Figure 1:
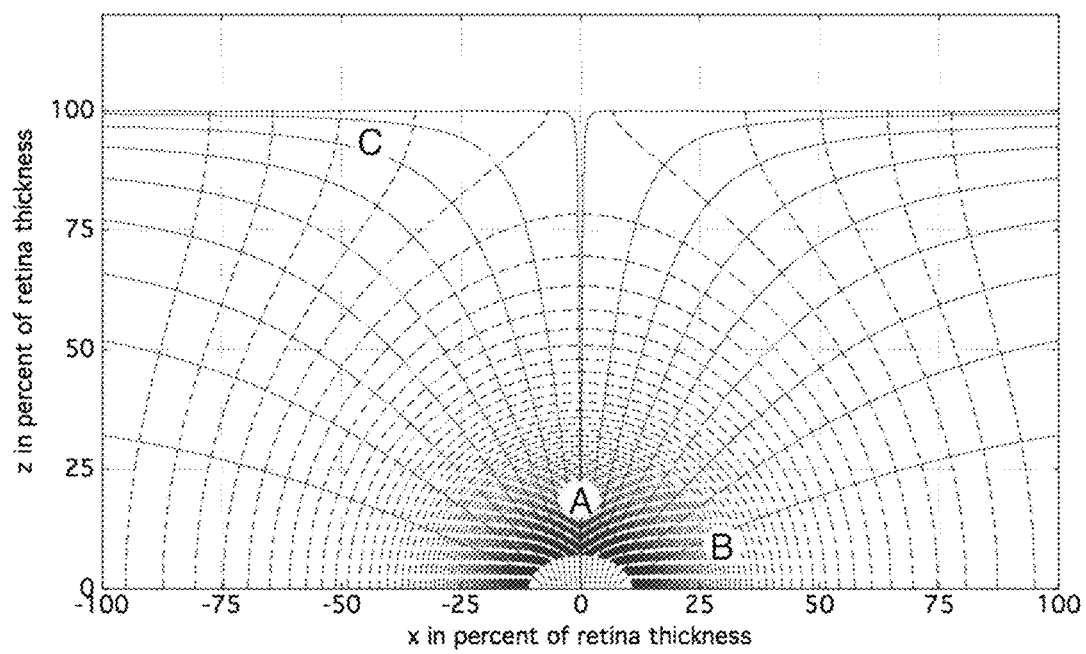
FIG. 1 is a graph showing a typical stimulation field produced by one activated electrode in sub-retinal position. In this graph, the counter electrode is at infinity, the vitreous is replaced by silicon oil. The electric current field is shown in solid red lines, the equipotential electric field is shown in broken blue lines; the density of blue lines is proportional to the strength of the current. The letters A, B and C mark typical target volumes for the stimulation of bipolar cells, dendritic connections, or neural networks in the ganglion cell layer, respectively.

The terms "stimulating electric field producing electrode" and "stimulating electrodes" are used interchangeably herein and refer to an electrode whose actuation by the controller results in an electric field that is sufficient to stimulate a neural cell or retinal tissue or any suitable cell in the neural pathway. It should be noted that in electrodynamics, field lines of electric force fields or electric current fields have a direction going from an anode to a cathode. In most cases, the stimulating electric field producing electrode will be a cathode. However, the scope of the invention is not limited to having the stimulating electric field producing electrode being a cathode, as it can also be an anode depending on a particular application.

The term "counter electrode" in reference to the stimulating electric field producing electrode refers to an electrode having an opposite polarity relative to the stimulating electric field producing (SEFP) electrode. Thus, the presence of a counter electrode allows the apparatus to be net electric neutral or allows formation of a closed circuit.

The term "field shaping electrode" or "FS electrode" refers to an electrode whose actuation by the controller results in an electric field that increases electric field strength near the vicinity of the cell to be stimulated and/or shapes the electric field produced by the SEFP electrode such that the stimulating electric field strength experienced by the cell is higher than the stimulating electric field strength experienced by the cell in the absence of actuation of the FS electrode under the same or substantially similar conditions. It should be noted that the strength of the stimulating electric field is increased because the guiding electric field "pushes" or forces the stimulating electric field into the target area that is to be stimulated. While it is intuitively obvious, it should be noted that the polarity of the FS electrode is same as the SEFP electrode.

The term "counter field shaping electrode" or "counter FS electrode" refers to an electrode having an opposite polarity relative to the field shaping (FS) electrode. Thus, the presence of counter FS electrodes in combination with the FS electrodes allows the apparatus of the invention to be net electric neutral or allows formation of a closed circuit.

The terms "transverse electrical field", "transverse stimulation electric field" and "transverse stimulation" are used interchangeably herein and refer to transverse electric field stimulation achieved using a high voltage but extremely short pulse duration. Transverse stimulation modality comes about by the shock-like nature of the electric stimulation in the short pulse range. The duration of stimulation using a transverse stimulation (or transverse electric field) is typically less than 20 μsec, often 10 μsec or less, and more often 1 μsec or less. While the applied voltage (i.e., voltage surge) is high in a transverse stimulation, due to the extremely short pulse duration, the actual transferred electric charge per transverse stimulation can be orders of magnitude smaller than the one transferred per longitudinal stimulation. Generally, a transverse stimulation is accompanied by a relatively prolonged rest period before the next transverse stimulation. Typical, the rest period between each transverse stimulation is about 50 μsec or more, often 100 μsec or more, more often 200 μsec or more, and most often 300 μsec or more.

The term "longitudinal electric field" or "longitudinal stimulation" refers to stimulation electric field that is parallel with respect to the axis of the axon or the dendrite that is being stimulated. Typically, longitudinal electric stimulation is achieved using a relatively low voltage (as compared to a transverse stimulation) with a relatively long pulse duration. The pulse duration of longitudinal stimulation is typically about 20 μsec or more, often 100 μsec or more, more often 200 μsec or more, and most often 300 μsec or more.

It should be appreciated that regardless of the type of stimulation used (e.g., longitudinal or transverse stimulation), the amount of voltage and/or the electric charge transferred per stimulation is sufficiently low enough to avoid causing any cell damage or death.

Unless context requires otherwise, the term "impaired electrical activity" in reference to a cell, a neural pathway or vision includes missing or disrupted electrical activity that results in the observed abnormality within the subject (e.g., a clinical condition in a subject).

The term "electric field" typically refers to a field of force surrounding a charged particle within which another charged particle experiences a force. However, for the purposes of the present disclosure, the term can also include electric current.

Apparatus of the Invention

As stated above, the apparatus of the invention can be used to directly stimulate a cell with impaired electrical activity. Typically, the apparatus of the invention is used to stimulate an intact (i.e., functioning) cell and/or intact pathway to "replace" or approximate the function of the cell that has impaired electrical activity or impaired electrical pathway. For example, some clinical conditions, such as blindness and paralysis, are caused by the loss of cells, e.g., rods and/or cones, and by a disconnected neural pathway (paralysis), respectively. The apparatus of the invention is typically used to stimulate the remaining intact cells and intact pathways to "replace" or approximate the function of the dead or impaired or missing cells or disconnected pathways.

Some aspects of the invention provide an apparatus that includes: an array of electrodes, wherein said array of electrodes comprises an arrangement of individual electrodes; and a controller operatively connected to said array of electrodes for actuating the individual electrodes, wherein said controller is configured to actuate at least one of the individual electrodes as a stimulating electric field producing electrode and at least one of the individual electrodes as a counter electrode having an opposite polarity relative to said stimulating electric field producing electrode, and wherein said controller is further configured to actuate said stimulating electric field producing electrode with a time profile adapted to produce a transverse stimulation electric field to a cell.

Yet in other embodiments, said controller is further configured to actuate at least one of the individual electrodes as a field shaping (FS) electrode to produce a guiding electric field and at least one other of said individual electrodes as a counter field shaping ("counter FS") electrode having an opposite polarity relative to said field shaping electrode such that the guiding electric field increases the strength of the transverse stimulation electric field to the cell relative to the strength of the transverse stimulation electric field to the cell in the absence of said guiding electric field.

Still in other embodiments, said controller is further configured to use a different electrode as a stimulation electric field producing electrode from the immediately preceding stimulation signal producing event.

Another aspect of the invention provides an apparatus comprising: an array of electrodes configured to be implanted in a subject; and a controller operatively connected to said array of individual electrodes and adapted for actuating said individual electrodes, wherein said controller is configured to actuate at least one of the individual electrodes as a stimulating electric field producing electrode to produce a cell stimulating electric field and at least one other of said individual electrodes as a field shaping electrode to produce a guiding electric field, wherein the presence of said guiding electric field increases the strength of said stimulating electric field to the cell relative to the strength of said stimulating electric field to the cell in the absence of said guiding electric field. As stated above, increase in the strength of the stimulating electric field is due to the guiding electric field "pushing" or forcing the stimulating electric field into the target area that is to be stimulated.

In some embodiments, said controller is configured to actuate said stimulating electric field producing electrode to produce a transverse stimulating electric field to the cell.

Yet in other embodiments, said field shaping electrode comprises a plurality of individual electrodes.

Still in other embodiments, said controller is further configured to actuate at least one of the individual electrodes as a counter electrode having an opposite polarity relative to said stimulating electric field producing electrode.

In other embodiments, controller is configured to actuate at least one of the individual electrodes as a counter field shaping electrode having an opposite polarity relative to said field shaping electrode.

In further embodiments, said controller is configured to actuate said field shaping electrode such that the duration of said guiding field is longer than the duration of said stimulation signal.

In some embodiments, the area near the vicinity of the SEFP electrode has an electrical field that is confined and relatively strong (as compared to the electric field near the vicinity of the counter electrode) such that it creates a narrow pixel representation or focused electric field. In the area near the vicinity of a counter electrode, the electric field can be diffused and relatively weak (as compared to the electric field near the vicinity of the SEFP electrode).

Another aspect of the invention provides an apparatus comprising an array of electrodes as disclosed herein and a controller that is configured for local area scanning.

Still another aspect of the invention provides an apparatus comprising an array of electrodes as disclosed herein and a controller that is configured for a Stochastic Optimization Framework.

A. Array of Electrodes

The apparatus of the invention includes an array of electrodes. Typically, these electrodes can be individually or independently controlled by the controller. The number of electrodes can vary depending on a particular application. For example, for stimulation of the retina, the number of electrodes in the array is typically at least 16 (4×4), often at least 60 (6×10), and more often at least 1500 (e.g., 39×39). An array of electrodes that is suitable for implantation is well known to one skilled in the art and some are currently available, such as from Bionic Vision (Australia), Second Sight Medical Products LLC (USA), and Retina Implant AG (Germany).

The array of electrodes is typically in a two-dimensional arrangement. It should be appreciated, however, that a plurality of arrays of electrodes can be used. For example, in treating vision impairment, three electrode arrays (each in a two-dimensional arrangement) can be simultaneously implanted to a subject suffering from vision impairment, for example, one in epi-retinal, one in sub-retinal, and one in supra-choroidal position. This assembly could be considered a 3-dimensional arrangement.

B. Controller

Typically a controller is operatively connected to a camera or video recorder external to the eye, or an intraocular camera, and an image processing device. However, in some instances, the controller does not depend on an image processing device but can be activated by the light or image entering a subject's retina.

A controller is typically a central processing unit containing device that can be programmed to actuate an electrode with a prescribed time-profile of actuation. The controller can also include various algorithms, for example, (i) to optimize the transverse stimulation electric field for a particular application based on a feedback system or an input from a user or an operator, (ii) utilize local area scanning process, which is discussed in detail below, (iii) perform electric field shaping through guiding fields, or (iv) any combination of the above.

Unlike conventional controllers, the controller of the invention is configured to actuate a SEFP electrode to produce a transverse stimulation electric field to the cell. In other embodiments, the controller of the invention is configured to actuate at least one electrode (i.e., SEFP electrode) to produce a stimulating electric field and at least one other electrode, typically a plurality of other electrodes (i.e., field shaping electrodes) to produce a guiding electric field (i.e., "guiding field"). Still in other embodiments, the controller of the invention is configured for local area scanning. Yet in other embodiments, the controller is configured to achieve two or more of the activities described above, i.e., production of transverse stimulation, guiding field production, and local area scanning. Furthermore, in some embodiments, the controller is configured to actuate a corresponding number of electrodes as a counter electrode and/or counter field shaping electrodes such that the array itself is a net electric neutral or closed circuit.

Local area scanning by the controller can be achieved, for example, by subdividing the entire area of the electrode array of an implant into at least one local area, typically a plurality of local areas. Each local area comprises a number of electrodes. In some embodiments, a local area comprises at least four electrodes, typically at least six electrodes, often at least ten electrodes, more often at least twenty electrodes, and most often at least 50 electrodes. However, it should be appreciated that each local area does not have to be the same size, i.e., each local area does not have to have the same number of electrodes. The sum of all electrodes in all local areas is smaller or equal to the total number of electrodes on the array.

A multipole (e.g., a 25-pole) is a chosen configuration of a certain number of electrodes that are used to generate one image-giving pixel (i.e., one stimulating electric field producing element). Some of these electrodes are used for producing the guiding field and some others are used for producing the stimulating electric field. It should be appreciated that a multipole can have a minimum of 2 electrodes and a maximum of all electrodes on the electrode array.

In each local area, the same or a different multipole configuration can be used. This means in particular: (1) that typically, but not necessarily, two local areas have the same multipole configuration, and (2) that the multipole configuration within a local area may change. Typically, a chosen multipole configuration for a particular local area scans the electrode positions in that local area as best as possible. However, if the local area is along the boundary of the electrode array, the multipole configuration is modified accordingly (some electrodes for that multipole are simply missing). If the multipole scans along the boundary to another adjacent local area, it adopts electrodes of that adjacent local area.

Each local area can, but not necessarily, consist of at least as many electrodes as there are in the multipole configuration chosen for stimulation and field shaping.

Utility

Other aspects of the invention provide a method for treating a clinical condition associated with an impaired electrical activity of a cell in a subject. Such method includes: implanting an apparatus of the invention to the subject at or near the site of a cell with impaired electrical activity; actuating said stimulating electric field producing electrode using said controller to produce a transverse stimulating electrical field from said stimulating electric field producing electrode thereby electrically stimulating the cell to treat the clinical condition associated with impaired electrical activity of a cell in said subject. As stated above, unless context requires otherwise, the term "impaired electrical activity" can include missing or disrupted electrical field communication or signaling from one cell to another. Moreover, the apparatus of the invention is typically implanted to electrically stimulate the intact (i.e., functioning) cells and intact pathways to "replace" or approximate the function of the cells that have impaired electrical activity or impaired electrical pathways.

Still other aspects of the invention provide a method for treating a clinical condition associated with an impaired electrical activity of a cell in a subject by actuating said stimulating electric field producing electrode and field shaping electrode using said controller to produce a stimulating electric field thereby electrically stimulating a cell within said subject to treat the clinical condition associated with impaired electrical activity of a cell.

In one particular embodiment, the clinical condition associated with an impaired electrical activity of the cell comprises vision impairment, stroke, spinal cord injury, peripheral nerve injury, demyelinating disease, or a combination thereof.

Yet in other embodiments, the clinical condition associated with an impaired electrical activity of the cell comprises vision impairment, multiple sclerosis, ameliorated lateral sclerosis, central nervous system injury, Parkinson's disease, Alzheimer's disease, paralysis (e.g., any kind of paralysis that can be treated by intramuscular stimulation), or a combination thereof.

Still in other embodiments, said controller generates a stimulating electric field using a different electrode as a stimulating electric field producing electrode from the immediately preceding stimulating electric field producing event.

Methods and apparatuses of the invention are applicable to the stimulation of other tissue/nerve regions, e.g., optic nerve, lateral geniculate nucleus (LGN), visual cortex, deep brain, and paralyzed limbs.

Discussion

While apparatuses and methods of the present invention can be used to treat any clinical condition associated with impairment in electrical stimulation or electrical signaling (e.g., electrical potential signaling) of cells and/or tissues, for the sake of brevity and clarity, the invention will now be described with reference to treating vision impairment. However, it should be appreciated that the scope of the invention is not limited to treating vision impairment, but is applicable to any clinical conditions that can be treated via electrical stimulation of cells and/or tissues.

Generally, there are two kinds of electric stimulation that can be used to treat a clinical condition associated with impairment in electrical stimulation of a cell: a transverse stimulation and a longitudinal (i.e., non-transverse) stimulation. Cells and tissues are very complicated electric conductors. Cells can be considered to be partly an electrolyte, partly an insulator, and/or partly a colloid. Cells contain macromolecules with various polarizabilities and have a complicated structure in space, with cells and clefts in between the cells.

The stimulation process of a nerve cell is a non-linear operator in mathematical language. For the analysis of experimental results, Fourier transformations are commonly used. A non-linear operator does not commute with these transformations. This means that stimulation cannot be studied in Fourier decomposition.

Theoretical descriptions of electric currents in tissues and theoretical descriptions of the stimulation process of cells are typically based on simplified models, such as continuum models, statistical models, suspension of spherical cells in an electrolyte model, etc. These models are useful as a basis for intuitive descriptions, and they are useful for designing experiments.

The standard model of electrical stimulation is based on the findings of Hodgkin and Huxley about the electric properties of nerve cells (e.g., [Hodgkin et al., *J. Physiol.* 1952, 117, 500-544]) and on Heaviside's cable equation. The original cable equation describes the gradual loss of a telegraph signal in an ocean cable. It also describes the situation when the signal travels in the ocean and the cable picks it up like an antenna; only the driving term of the equation is different in the two cases. When a dendrite or an axon has the mathematical properties of a cable, Heaviside's equation is also valid in a continuum model of a nerve tissue such as the retina.

Unlike conventional electrical stimulation devices used for stimulating neurons or retinal tissue, an apparatus and a method of the invention use transverse stimulation of a cell and/or tissue to treat a clinical condition associated with electrical stimulation impaired cells and/or tissues, e.g., perpendicular to the axon or dendrite of a nerve cell.

In conventional electrical stimulation devices that are used to stimulate neurons or retinal tissue, a sustained ohmic current is produced between an electrode and a counter electrode by a so-called voltage-controlled generator or a current-controlled generator. A voltage-controlled generator typically applies a constant voltage of a few volts for a time interval typically somewhere between 0.3 and 3 milliseconds. The current, after reaching a maximum, decreases while the Helmholtz-layers of the electrodes are charging up. In contrast, a current-controlled generator keeps the current at a substantially constant value. In both cases, care is taken to avoid irreversible chemical reactions. In the first case, the applied voltage is set accordingly low, in the second case, the injected (i.e., applied) charge is limited by choosing a small current and a short enough time interval. Suitable voltage and current for a particular application are well known to or can be readily determined by one skilled in the art.

Except for the very beginning of charge injection, in some embodiments the controller of the invention applies a sustained ohmic current flowing along the clefts between the cells of the retina. In the underlying continuum model, the clefts and cells of the retina are smeared out, except for the nerve cell under consideration. When the current has a longitudinal (i.e., parallel) component with respect to the axis of the axon or the dendrite under consideration, its electric field enters the nerve cell. This process is described by the antenna-version of Heaviside's cable equation.

It has been a long accepted belief that a cable model for stimulation needs a longitudinal current for the stimulation of a non-myelinated axon or a dendrite. It has also been generally accepted that a transverse (i.e., perpendicular) electric current or field cannot stimulate in the cable model. However, Fried et al. searched for sections of an axon emerging from a retinal ganglion cell that are especially sensitive to electrical stimulation. Fried et al., *J. Neurophysiol.*, 2009, 101, pp. 1972-1987. Briefly, Fried et al. placed a conical electrode into the retina, sideways from an axon and pointing toward the axon (i.e., perpendicular to the axon), and injected a constant current for the rather short time of 100-200 microseconds, and observed that the transverse current stimulated the axon.

The cable model does not fully explain Fried et al.'s observation. There has been an ohmic current for 100 microseconds. But this current was aiming at the spot in which the investigators were interested, i.e., had a direction perpendicular to the axon. Only farther away from that spot it did have a longitudinal component. The sharp onset of charge injection with the rectangular time profile of the current produced a sufficiently strong voltage surge for a transverse stimulation. The rest period needed for the transverse stimulation had been set to 10 milliseconds and was part of the time profile.

Thus, for the operation of a retinal implant, transverse stimulation is an excellent alternative to longitudinal stimulation. An injected charge-controlled generator, instead of a voltage-controlled or current-controlled one, is more suitable for transverse stimulation. As discussed above, to achieve transverse stimulation, it is important that the charge is injected very fast—termed flash or shock stimulation—faster than relaxation, and without any significant voltage bound. This means that the energy needed is stored before injection in the circuitry of the generator (e.g., in a capacitor). Injection may be repeated after the relaxation current has decreased from its maximum value to some given lower value, before discharging the electrode. In some embodiments, electric field shaping is used to stimulate the target cells.

Stochastic Stimulation

Stochastic stimulation of the retina takes place when the stimulation current in extracellular space interferes with the omnipresent synaptic noise of a neural network. Synaptic noise is known from the cortex of the brain; it is believed to be present also in the ganglion cell layer of the retina. The term "noise" means "non-directional" or "no transport of information". A small electric field may be sufficient to make such noise "directional", i.e., transporting information. In the retina such primitive information might be perceived as a phosphene. There is a similarity to the Maxwell-Boltzmann velocity distribution of gas molecules: a very small deviation from a spherical, isotropic distribution is macroscopically observed as "wind", i.e., directional. The magnitude of an electric current sufficient to cause a phosphene is expected to be small, typically smaller than the current needed for longitudinal stimulation. We expect such phosphenes to appear, for instance, in area C of FIG. 1.

The area around A in FIG. 1 is the ideal target volume for the stimulation of bipolar cells by a longitudinal field. In the target volume B of FIG. 1, one finds bipolar cells for transverse stimulation or dendritic connections. In the target volume C one expects to find neural networks of the ganglion cell layer. Depending on the type of stimulation one would like to "aim" at such target volumes, i.e., one would like to have a strong stimulation field in that volume and a less strong field elsewhere.

Unfortunately, an electric current cannot be focused like a laser beam. The electric current field has to satisfy the Poisson equation, and there is a non-crossing rule of field lines: what is true for electric currents is also true for electric fields. If field shaping is desired, means or methods that are consistent with these rules must be utilized.

Field Shaping Using a Guiding Field

When an electric field or a current field is produced by an array of electrodes, every field line goes from exactly one of the anodes to one of the cathodes. A neighboring line at infinitesimal distance goes from the same anode to the same cathode. There are areas, however, in which field lines emerge from another anode and/or go to another cathode. Every two of such areas are separated from each other by a mathematical surface called "separatrix." See, for example, see Lehner in *Elektromagnetische Feldtheorie für Ingenieure und Physiker*, Springer 1990, ISBN 3-540-52319-7.

The position and shape of such separatrices are determined by the geometry of electrode positions and by the activation potentials. Some aspects of the invention use one or more field shaping electrodes to produce guiding fields for shaping the stimulating electric field.

Figure 2A:
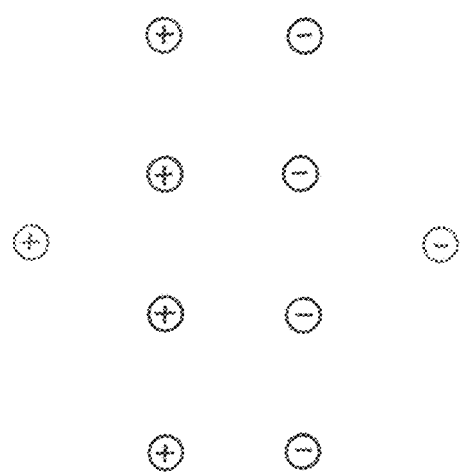
FIGS. 2A-2C show how the stimulating electric field in red is shaped (i.e., pushed up or forced) by a guiding field of the shape of a ridge built by 4 dipoles (i.e., field shaping electrodes).
Figure 2B:
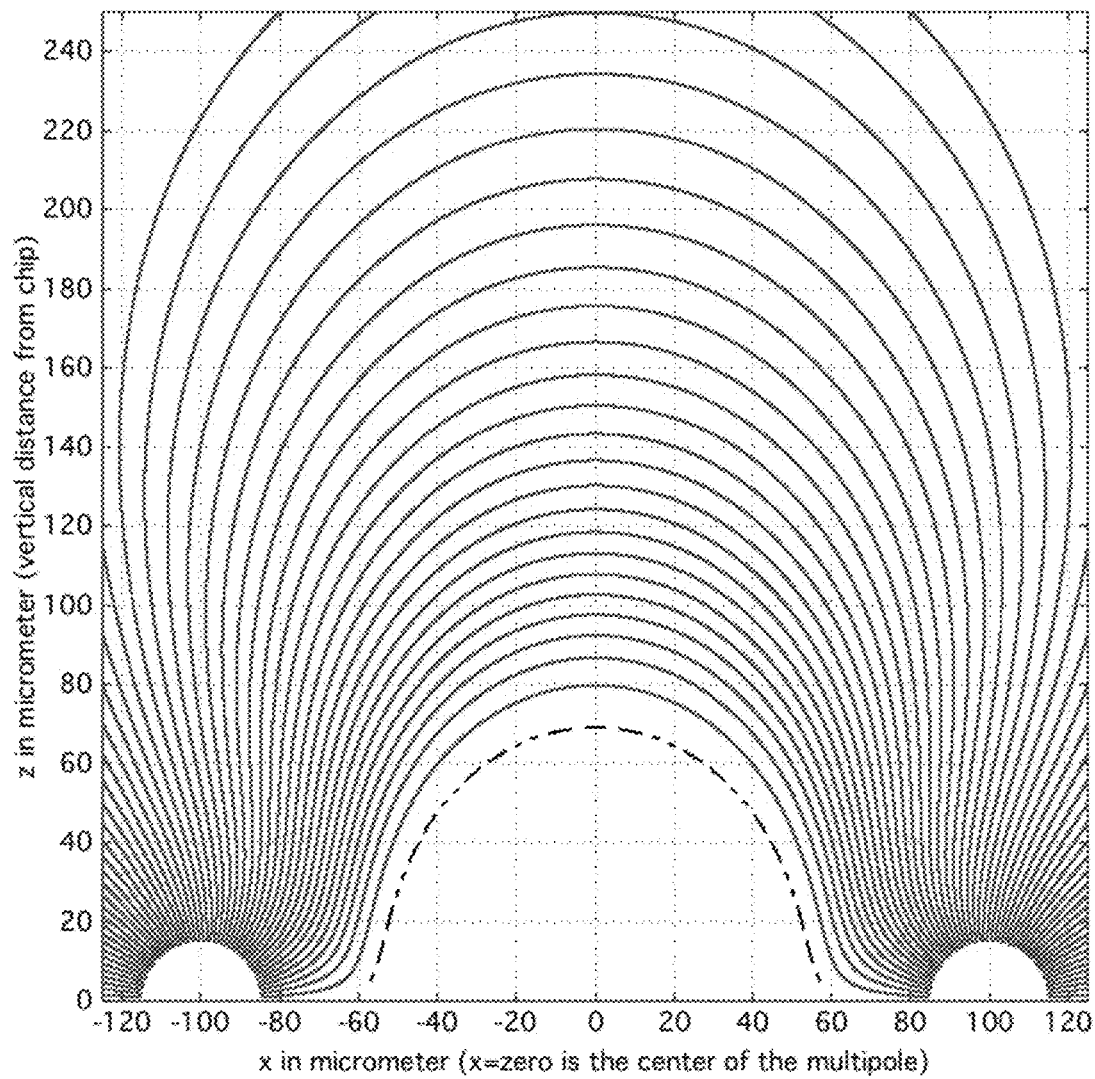
Figure 2C:
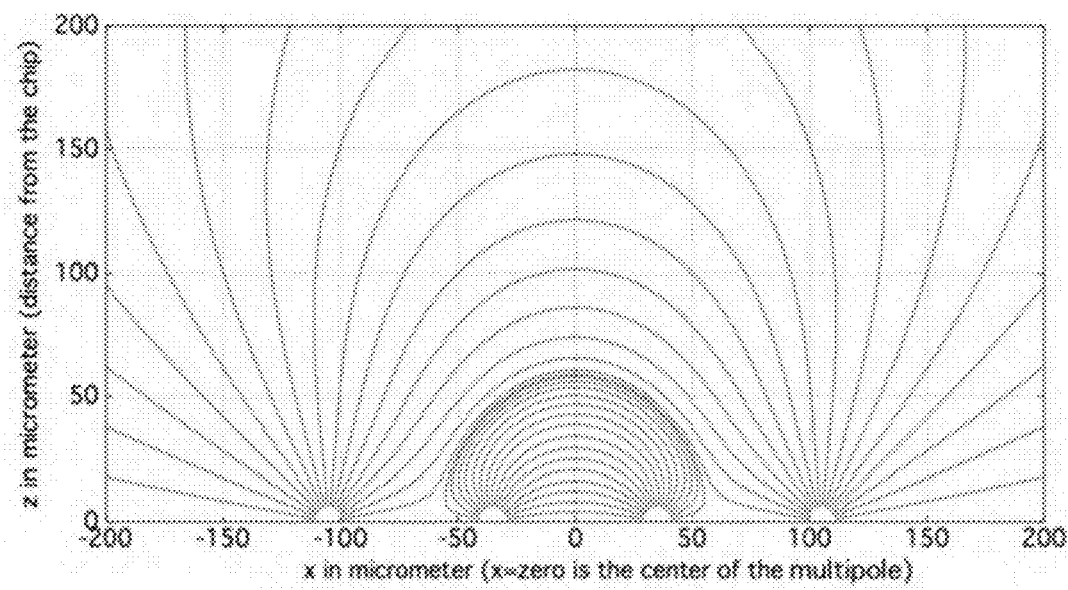

For example, a separatrix has been simulated that has the form of a ridge. It is formed by an arrangement of electric dipoles (i.e., electrodes). See FIG. 2. The direction of the dipoles is perpendicular to the ridge. The ridge has peaks and saddles. The stimulating electric field producing electrode is situated in front of the ridge, its counter electrode is situated behind the ridge as can be seen in FIG. 2A. The surface of the ridge is the separatrix (i.e., separation of the stimulation field from the guiding field) for the stimulating electric field. The field between SEFP electrode and counter electrode cannot penetrate into the ridge (i.e., guiding field) because of the non-crossing rule of electric field lines, it has to "climb over it." Thus, the stimulating electric field density is high near a saddle. An example of stimulating electric field lines is shown in FIG. 2B. The highest point of the separatrix is a saddle in this figure. The field lines in close vicinity of the stimulating electrode are not shown for plotting reasons. The guiding field lines between the field shaping electrodes of the dipoles (shown in blue in FIG. 2A) fill the space between the separatrix and the x-axis, i.e., underneath the separatrix. They are considered as an auxiliary field (i.e., guiding field) and are not shown in FIG. 2B. They are shown in FIG. 2C.

The guiding field is not supposed to stimulate cells. This is achieved by giving it another time profile compared to the stimulating electric field. For predominantly transverse stimulation, for instance, this is achieved by choosing a time profile of the auxiliary current (i.e., guiding field) that yields a predominantly longitudinal stimulation.

Multipoles Formed by Stimulating Electrodes and Field Shaping Electrodes

An example of using several electrodes of an array for guiding a stimulating electric field to a prescribed target volume is illustrated in FIG. 2. Four dipoles i.e., 8 electrodes, are used to form a guiding field plus 2 electrodes for stimulation (FIG. 2A). The configuration is suitable for stimulation in target area B of FIG. 1. The distance of the target volume from the array of electrodes (i.e., chip) can be increased either by increasing the strength of the guiding field or by using field shaping electrodes that are farther apart from each other.

Figure 3A:
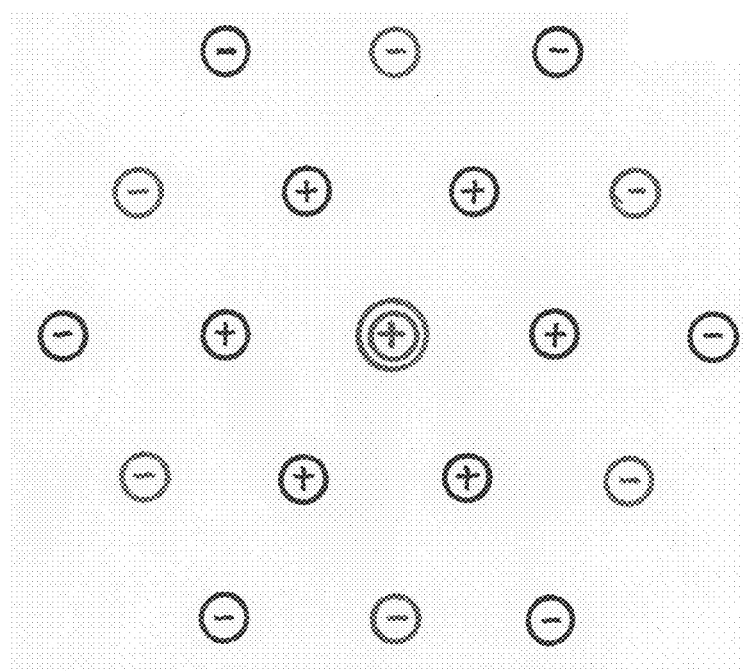
FIG. 3A illustrates one embodiment of a multipole consisting of 19 electrodes in a hexagonal array. The multipole represents one pixel. The stimulating electric field emerges from the center electrode and, for the chosen actuation, goes to the six counter electrodes shown in red. The electrodes shown in blue build up a guiding field of approximate ring-shape for shaping the stimulating electric field. The signs shown are given for anodic stimulation. For cathodic stimulation, the polarity is reversed.

In order to stimulate in target area A of FIG. 1, with a vertical current, a center electrode encircled by ridge forming dipoles is needed. One example of such a configuration is illustrated in FIG. 3A. The chip carries a hexagonal grid of electrodes. The electrodes forming the guiding field for the stimulating electric field are shown in blue. The stimulating electric field electrode in the center and the corresponding counter electrodes are shown in red.

Figure 4:
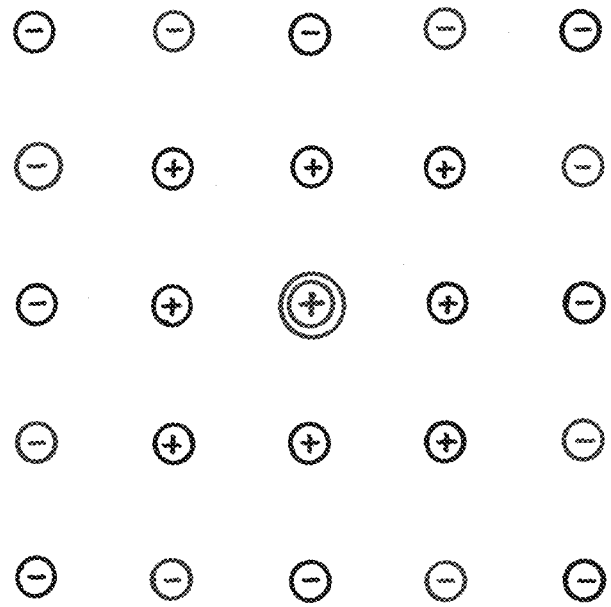
FIG. 4 illustrates a multipole consisting of 25 electrodes, in a quadratic array configuration. The multipole represents one pixel. In this example, the stimulating electric field emerges from the center electrode and goes to the eight counter electrodes shown in red. The electrodes shown in blue build up a guiding field of approximate ring-shape for shaping the stimulating electric field. The signs shown are given for anodic stimulation. For cathodic stimulation the signs (i.e., polarity) have to be reversed.

As shown in FIG. 3B, the stimulation electric field can be viewed as a fountain, rising in the middle, dividing up and falling down to the return (i.e., counter) electrodes. The configuration in FIG. 3A is a hexagonal grid of electrodes. Other configuration of electrodes can also be used. For example, a cubic configuration of electrodes as shown in FIG. 4 can also be used. Again, dipoles around a center electrode form a ridge (i.e., guiding field) for the stimulating electric field.

It should be noted that both the stimulating electric field and the guiding field are dynamic in nature, i.e., they change their respective shape over time (i.e., the separatrix changes its shape and location over time). For example, with a multipole, as depicted in FIGS. 3A and 4, the stimulating field emerges from the central electrode over time and forces itself like the central part of a fountain through the guiding electric field that forms a ridge, to ultimately bend back down above the ridge towards the counter electrodes.

Local Area Scanning Stimulation

The idea of imaging with an array of electrodes is to utilize as many pixels as there are electrodes, and not to use many electrodes for shaping an electric field. The latter is illustrated in FIG. 2, and more so in FIGS. 3 and 4.

Research on retinal implants is carried by the hope that the phosphenes produced by electrical stimulation are small and thus can be used as picture elements called "pixels". It would be ideal to have as many pixels as there are electrodes on the array. In some embodiments of the invention, the controller is configured for local area scanning stimulation such that the total number of pixels on the array of electrodes is same as the total number of electrodes present on the array.

In FIGS. 4 and 5, 25 and 19 electrodes are used for producing only one pixel, respectively. The center electrode is used for transmitting or producing the stimulating electric field and 24 (FIG. 4) or 18 (FIG. 5) electrodes are used as counter electrodes and field shaping electrodes. Without a local area scanning stimulation feature, there are too many electrodes for producing one single pixel such that only X/25 (where X is the total number of electrodes on the array) pixels are present on the electrode array, in both cases (25- and 19-pole). The 19-pole needs also a total of 25 electrodes, because the array cannot be patterned with 19-poles without gaps.

During the operation of a retinal implant it is desirable to avoid transmitting or producing only one single image. Correcting vision impairment requires the array of electrodes to provide a sequence of images similar to a video. Typically, a video has 25 frames of images per second. This allows for about 40 milliseconds to transmit one frame or image. This is more time than needed for completing an electrical stimulation process.

Figure 5:
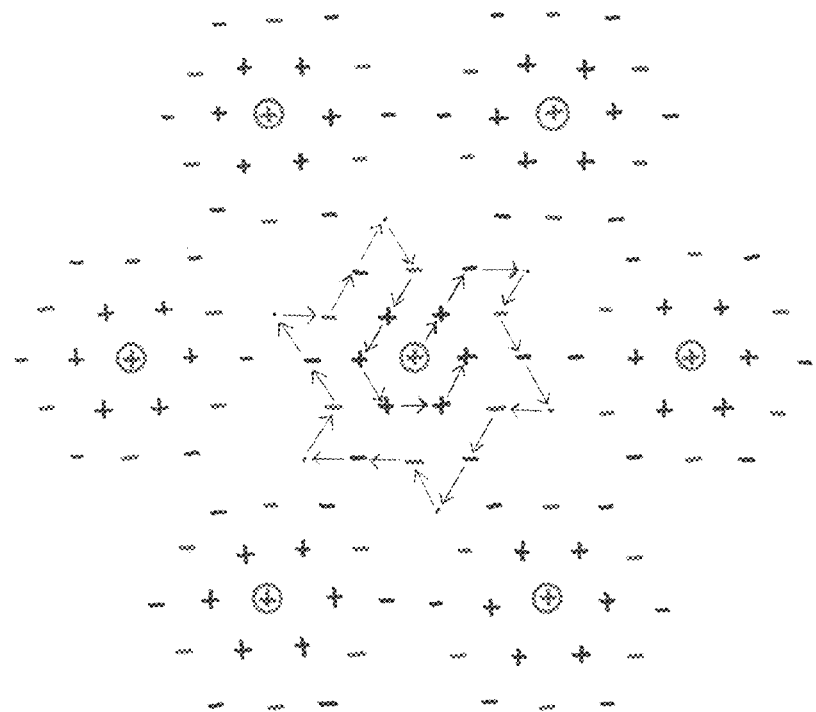
FIG. 5 illustrates an example of local area scanning stimulation with multipoles of the type shown in FIG. 3A. The centers of all multipoles jump after each stimulation or time slice to a new position on the hexagonal grid, as shown by arrows for the multipole in the center. The sequence of jumping is irrelevant as long as it covers all electrodes of the chosen local area within the time between two consecutive video frames.

For longitudinal stimulation the typical length of a monophasic voltage pulse is about 0.5 milliseconds. The resulting biphasic current pulse decays to a current density below stimulation threshold after about 0.8 milliseconds. The cell membrane needs some time to respond. Assuming the same amount of time for cell membrane's response, the stimulation process is completed after about 1.6 milliseconds. For transverse stimulation the stimulation process needs about a microsecond for charge injection and a rest period of up to 1 millisecond. Thus, a time window of 1.6 milliseconds is needed for completing a process of longitudinal stimulation and a little less for transverse stimulation. This means that there are at least 25 time slices for every one of the 40 millisecond frames of the video sequence. After each one of these 25 time slices, the allocation of electrodes to multipoles can be changed. Except for the boundary of the array, every electrode can become the center of a multipole like the ones shown in FIGS. 3A and 4. The change of allocation (i.e., local area scanning stimulation) is illustrated in FIG. 5, as an example. In this way, the full resolution of the electrode array is recovered, except for a potential loss along the boundary of the array. This loss along the circumference of an electrode array would favor circular over rectangular electrode arrangements, which would also conform better to the fundus. In case of the multipole shown in FIG. 4, the jumping sequence may be row-by-row, similar to a television screen if the overall electrode array had a rectangular arrangement of electrodes in rows and columns.

Transverse, Monopolar Stimulation with a Remote Counter Electrode

In cases where the desired stimulation volume is situated right on top of the electrode, with a stimulation diameter not larger than the electrode and a thickness of less than 100 μm, unipolar transverse stimulation with one large remote counter electrode can be used. An example of a transverse stimulation includes: (1) an extremely short charge injection (in the range of nanoseconds, up to a few microseconds), (2) a very small amount of injected charge (of less than 1 nC) and (3) a rather long rest period (of about 1 millisecond) after each charge injection. The occurrence of cross-talk during the short time of charge injection can easily be avoided. Cross-talk occurs whenever the actuation of a stimulation field producing multipole influences the stimulation field of another multipole. Some cross-talk may arise when a second electrode in close neighborhood actuates while the first electrode is still in its rest period. This can be avoided by randomizing the firing order, or in computer-controlled applications, it can be avoided by a computer algorithm that governs the stimulation sequence.

Stochastic Optimization Framework

A stochastic optimization framework can be employed for the spatio-temporal optimization of the electrode array (i.e., the spatial arrangements of the electrodes on the array) and the process of field shaping. The goals are: (a) to achieve optimal field shaping with a given electrode array (i.e., chip), (b) to optimally design the electrode array itself, i.e., to determine the spatial arrangement and size/diameter of the electrodes on the electrode array, and (c) to optimally drive the stimulation through a given, implanted electrode array in real time during usage of the retinal implant.

In 2008, one of the present inventors has introduced a Stochastic Optimization Framework (SOF) [see Fink, in "*Stochastic Optimization Framework (SOF) for Computer-Optimized Design, Engineering, and Performance of Multi-Dimensional Systems and Processes*," Proc. SPIE, 2008, Vol. 6960, 69600N; DOI:10.1117/12.784440] that allows optimizing a system or process that is governed by numerous adjustable parameters. The underlying principle is the minimization of a fitness function that measures the difference between a desired outcome and an actual outcome while operating the system or performing the process. The minimization of this fitness function is accomplished via multi-dimensional stochastic optimization algorithms, such as Simulated Annealing (see, for example, Metropolis et al., *J. of Chem. Phys.*, 1953, 21, pp. 1087-1091, 1953; and Kirkpatrick et al., *Science*, 1983, 220, pp. 671-680), Genetic Algorithms (see Goldberg in *Genetic Algorithms in Search, Optimization and Machine Learning*, Addison-Wesley, 1989), and other Evolutionary Algorithms. The common characteristic of these algorithms is the capability to escape local minima of a fitness function while approximating (and ideally reaching) the global minimum. This characteristic is in stark contrast to deterministic, gradient-descent-based algorithms, such as the Levenberg-Marquardt algorithm (see, for example, Press et al., *Numerical Recipes in C: The Art of Scientific Computing*, Cambridge University Press, Cambridge, N.Y., 1991, pp. 286-289), which tend to be poor performers in multi-dimensional landscapes that exhibit multiple local minima and are locally rugged. The stochastic optimization algorithms use as their input the fitness function value for each iteration and generate a new, modified set of parameter values as a result, ultimately converging to a set of parameter values that yields the desired fitness function value, e.g., close to zero.

The Stochastic Optimization Framework has been applied to the optimization of prosthetic vision, in particular provided by epi-retinal implants, to manipulate electric stimulation parameters of an implanted epi-retinal electrode array to optimize the resulting visual perception of the blind subject. See Fink et al., "*Stochastic Optimization Framework for the Optimization of Prosthetic Vision*," ARVO (Association for Research in Vision and Ophthalmology), 2008 Conference, Ft. Lauderdale, Fla., Invest. Ophthalmol. Vis. Sci. 2008, 49, E-Abstract 1779, abstract and poster; and Fink et al., Patient-in-the-loop Optimization of Prosthetic Vision; Neural Interfaces Conference, Long Beach, Calif., Jun. 21-23, 2010. See, also, U.S. Pat. Nos. 7,321,796; 8,078,309 and 8,260,428.

In a similar manner, the SOF can be applied to the following optimization scenarios:

1. Optimal field shaping with a given electrode array (i.e., chip): A given electrode array means that the spatial location and specifications for each electrode (e.g., diameter, electrode material) are fixed. The SOF can be used to optimize the current through the various electrodes such that the resulting 3D shape of the electric field approximates within user-defined tolerances the desired one. The 3D shape of the electric field can be accurately simulated as described in Schmid et al., "*Electric Stimulation of the Retina*," 2010, arXiv:1012.5958v1 [q-bio.NC]. The underlying electrostatic model of the electrode array provides the fitness function necessary for the SOF.

2. Optimal electrode array design: This scenario is an extension of the first one above. Here the constraint of having a spatially fixed electrode arrangement is relaxed, and the SOF is employed twice: (1) in an outer optimization loop, optimizing the spatial location/arrangement and even the specifications for each electrode (e.g., electrode diameter), and (2) in an inner optimization loop, performing the electric current optimization as described in scenario 1. The result is an optimized electrode array design.

3. Real-time stimulation optimization: Using a sufficiently capable miniaturized computing system one can perform the SOF-based optimization described in scenario 1 in real time (i.e., during actual usage of the vision prosthesis) given the fixed geometry and specifications of the implanted electrode array and the electrostatic model of the electrode array to generate the fitness function for the SOF. With prior image processing of the camera images that feed into the artificial vision implants (especially retinal implants) one can estimate what the desired 3D shape of the electric field for each individual time slice for a processed camera frame should be. This makes a comparison of the resulting 3D shape of the electric field across the electrode array during the SOF-based optimization process and the desired 3D shape possible, thus delivering the fitness function. Note, that all of this happens prior to the actual electric stimulation of each time slice for a camera frame via the electrode array: only the respective current profiles of all electrodes underlying the sufficiently converged 3D shape of the resulting electric field corresponding to each time slice of the image-processed camera frame are stimulated before the time slices for the next camera frame are processed accordingly.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. An apparatus for electrically stimulating a cell, said apparatus consisting of:
   a plurality of electrodes; and
   a controller operatively connected to said plurality of electrodes,
   wherein said controller is configured to actuate a first electrode to produce a transverse stimulation electric field having a duration of less than 20 µsec to a cell, and wherein said first electrode comprises at least one of said plurality of electrodes.

2. The apparatus of claim 1, wherein said controller is further configured to actuate a second electrode as a counter electrode having an opposite polarity relative to said first electrode, and wherein said second electrode comprises at least one other of said plurality of electrodes.

3. The apparatus of claim 1, wherein said controller is further configured to actuate:
   a third electrode to produce a guiding electric field, wherein said third electrode comprises at least one of yet another of said plurality of electrodes; and
   a fourth electrode as a counter electrode having an opposite polarity relative to said third electrode such that said guiding electric field increases the strength of said transverse stimulation electric field to the cell relative to the strength of said transverse stimulation electric field to the cell in the absence of said field-shaping guiding electric field, wherein said fourth electrode comprises at least one of yet another of said plurality of electrodes.

4. The apparatus of claim 1, wherein said controller is further configured to produce a subsequent transverse stimulation electric field using an electrode that is different from the electrode that is used to produce the immediately preceding transverse stimulation electric field.

5. An apparatus for electrically stimulating a cell, said apparatus consisting of:
   a plurality of electrodes; and
   a controller operatively connected to said plurality of electrodes, wherein said controller is configured to actuate:
      (i) a first electrode to produce a cell stimulating electric field having a duration of 20 µsec or less, wherein said first electrode comprises at least one of said plurality of electrodes; and
      (ii) a second electrode to produce a guiding electric field, wherein said second electrode comprises at least one other of said plurality of electrodes,
   wherein the presence of said guiding electric field increases the strength of said cell stimulating electric field relative to the strength of said cell stimulating electric field in the absence of said guiding electric field.

6. The apparatus of claim 5, wherein said controller is configured to actuate said first electrode to produce a transverse stimulating electric field to the cell.

7. The apparatus of claim 5, wherein said controller is configured to actuate said first electrode to produce a transverse stimulating electric field using a Stochastic Optimization Framework.

8. The apparatus of claim 5, wherein said controller is configured to actuate said second electrode to produce said guiding electric field using a Stochastic Optimization Framework.

9. The apparatus of claim 5, wherein said controller is further configured to actuate:
   a third electrode as a counter electrode having an opposite polarity relative to said first electrode, wherein said third electrode comprises at least one other of said plurality of electrodes, and
   a fourth electrode as a counter electrode having an opposite polarity relative to said second electrode, wherein said fourth electrode comprises at least one of yet another of said plurality of electrodes.

10. The apparatus of claim 5, wherein said controller is further configured to produce a subsequent cell stimulating electric field using an electrode that is different from the electrode that is used to produce the immediately preceding cell stimulating electric field.

11. The apparatus of claim 5, wherein said controller is configured to produce said guiding electric field that is longer in duration than said cell stimulating electric field.

12. A method for treating an impaired electrical activity of a cell, said method consisting of stimulating a cell having impaired electrical activity using an apparatus of claim 1 to treat said impaired electrical activity of said cell, wherein said stimulation of the cell comprises producing a transverse cell stimulating electric field having a duration of 20 µsec or less.

13. The method of claim 12, wherein said apparatus of claim 1 is implanted within said subject near the site of said cell with impaired electrical activity.

14. The method of claim 12, wherein a clinical condition is associated with said impaired electrical activity of a cell.

15. The method of claim 14, wherein said clinical condition comprises vision impairment, stroke, spinal cord injury, peripheral nerve injury, demyelinating disease, or a combination thereof.

16. The method of claim 14, wherein said clinical condition comprises multiple sclerosis, ameliorated lateral sclerosis, central nervous system injury, Parkinson's disease, Alzheimer's disease, paralysis, epilepsy, Homer syndrome, incontinence, schizophrenia, depression, or a combination thereof.

17. The method of claim 12, wherein said controller generates a cell stimulating electric field using a different electrode from the electrode used to produce the immediately preceding cell stimulating electric field.

18. The method of claim 12, wherein said transverse cell stimulating electric field is produced by said controller using a Stochastic Optimization Framework.

19. The method of claim 12, wherein said controller is further configured to actuate:
   a third electrode to produce a guiding electric field, wherein said third electrode comprises at least one other electrode; and
   a fourth electrode as a counter electrode having an opposite polarity relative to said third electrode, wherein said fourth electrode comprises at least one of yet another electrode, wherein said guiding electric field increases the strength of said transverse cell stimulating electric field to the cell relative to the strength of said transverse cell stimulating electric field in the absence of said guiding electric field.

20. The method of claim 19, wherein said guiding electric field is produced by said controller using a Stochastic Optimization Framework.

\* \* \* \* \*